(12) United States Patent
Herrlich-Loos et al.

(10) Patent No.: US 7,790,638 B2
(45) Date of Patent: Sep. 7, 2010

(54) HUMIDITY-REGULATING COMPOSITE MATERIALS

(75) Inventors: Mirjam Herrlich-Loos, Mannheim (DE); Corinna Haindl, Mannheim (DE); Samantha Champ, Ludwigshafen (DE); Martin Beck, Maxdorf (DE); Markus Tönnessen, Ludwigshafen (DE); Michael Fastner, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 105 days.

(21) Appl. No.: 11/994,517

(22) PCT Filed: Aug. 9, 2006

(86) PCT No.: PCT/EP2006/065170

§ 371 (c)(1),
(2), (4) Date: Jan. 3, 2008

(87) PCT Pub. No.: WO2007/023086

PCT Pub. Date: Mar. 1, 2007

(65) Prior Publication Data

US 2008/0194162 A1   Aug. 14, 2008

(30) Foreign Application Priority Data

Aug. 23, 2005  (DE) .................. 10 2005 039 968

(51) Int. Cl.
*B32B 27/04* (2006.01)
*B32B 35/00* (2006.01)

(52) U.S. Cl. .................. 442/59; 442/181; 442/327; 428/500; 428/515; 428/844.6; 264/494

(58) Field of Classification Search ............. 442/59, 442/181, 327; 428/500, 515, 844.6; 264/494
See application file for complete search history.

(56) References Cited

U.S. PATENT DOCUMENTS

| 5,962,068 A | 10/1999 | Tsuchiya |
| 2004/0198114 A1 * | 10/2004 | Barnholtz et al. .............. 442/1 |

FOREIGN PATENT DOCUMENTS

| DE | 41 27 337 | 3/1992 |
| DE | 10 2005 015 536 | 10/2006 |
| EP | 1 178 149 | 2/2002 |
| GB | 2 376 695 | 12/2002 |
| JP | 05 105705 | 4/1993 |
| WO | WO-00/64311 | 11/2000 |
| WO | WO-01/56625 A2 | 8/2001 |
| WO | WO-2004/067826 | 8/2004 |

OTHER PUBLICATIONS

International Search Report in PCT/EP2006/065170 dated Nov. 2, 2006.
Buchholz et al., Modern Superabsorbent Technology, pp. 69-117 (1998).
U.S. Appl. No. 11/908,322.

* cited by examiner

*Primary Examiner*—Ula C Ruddock
(74) *Attorney, Agent, or Firm*—Marshall, Gerstein & Borun LLP

(57) ABSTRACT

The invention concerns improved moisture-regulating composites comprising a sheetlike substrate material, a water-soluble hygroscopic substance and a water-absorbing polymer polymerized onto the substrate material in the presence of the hygroscopic substance and comprising a plasticizer, methods of making them and their use for moisture regulation.

14 Claims, No Drawings

HUMIDITY-REGULATING COMPOSITE MATERIALS

CROSS-REFERENCE TO RELATED APPLICATIONS

This is the U.S. national phase application of International Application No. PCT/EP2006/065170, filed Aug. 9, 2006, which claims the benefit of German patent application No. 10 2005 039 968.1, filed Aug. 23, 2005.

The present invention relates to improved moisture-regulating composites, methods of making them and their use for moisture regulation.

Further embodiments of the present invention are discernible from the claims, the description part and the examples. It will be appreciated that the hereinbefore identified and the hereinafter still to be more particularly described features of the present invention's subject matter are utilizable not just in the particular combination indicated but also in other combinations without leaving the realm of the present invention.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products swellable in aqueous fluids, examples being guar derivatives. Such polymers are used as products capable of absorbing aqueous solutions to produce diapers, tampons, sanitary napkins or other hygiene articles, but also as water-containing agents in market gardening.

The prior art for the production of water-absorbing polymers is described in summary for example in the monograph "Modern Superabsorbent Polymer Technology", F. L. Buchholz and A. T. Graham, Wiley-VCH, 1998, pages 69 to 117.

WO 01/56625, EP-A-1 178 149 and U.S. Pat. No. 5,962,068 describe processes for producing water-absorbing composites in each of which water-absorbing polymers are polymerized onto a substrate material.

WO 00/64311 discloses composites wherein water-absorbing polymers were polymerized onto a substrate material. The composites are used for moisture regulation in seat padding. WO 2004/067826 A1 teaches multilayered textile fabrics, in particular those composed of nonwovens stitch bonded on one surface which may comprise active components such as water-absorbing polymers for example.

JP-A 05-105705 describes nondeliquescent driers consisting of a substrate material and hygroscopic salts wherein the hygroscopic salts are fixed to the substrate material by means of water-absorbing polymers.

Prior German patent application DE 10 2005 015 536.7 describes moisture-regulating composites comprising at least one sheetlike substrate material, at least one water-soluble hygroscopic substance and at least one water-absorbing polymer polymerized onto the substrate material in the presence of the water-soluble hygroscopic substance.

Existing moisture-regulating composites are frequently relatively stiff and the particles of water-absorbing polymers therein are relatively hard. This stiffness may give rise to difficulties in further processing and use of the composites and the drapability of the composites is adversely affected. In addition, where such moisture-regulating composites, usually used to avoid unpleasant effects associated with transpiration, come into local contact with larger amounts of liquid than are commonly produced by transpiration, for example when liquid is spilt onto seat furniture or autoseats equipped with such composites, undesirable unevennesses may appear, only to take longer to disappear again through drying than the customary drying of the moisture-regulating composites.

The present invention has for its object to provide moisture-regulating composites possessing good drapability.

We have found that this object is achieved by moisture-regulating composites comprising
a) at least one sheetlike substrate material,
b) at least one water-soluble hygroscopic substance, and
c) at least one water-absorbing polymer polymerized onto said substrate material a) in the presence of said substance b), the weight ratio of said hygroscopic substance b) to said polymer c) being in the range of 0.01 and 1, wherein the polymer c) comprises a plasticizer.

The ratio of hygroscopic substance b) to polymer c) is preferably less than 0.8, more preferably less than 0.6, even more preferably less than 0.5 and most preferably less than 0.4 and at least 0.05, more preferably at least 0.1 and even more preferably at least 0.15.

The substrate materials a) are not subject to any restriction. Preferred substrate materials are wovens and/or nonwovens as described in WO 01/56625 at page 16 line 40 to page 20 line 27, or hybrid forms composed of wovens and nonwovens as disclosed in WO 2004/067826.

Suitable substrate materials a) are for example wovens or nonwovens composed of synthetic polymeric fibers. The fibers may be made of any spinnable polymeric material, examples being polyolefins, such as polyethylene or polypropylene, polyesters, such as polyethylene terephthalate, polyamides, such as nylon-6 or nylon-6.6, polyacrylates, modified celluloses, such as cellulose acetate. Mixtures of abovementioned polymeric materials can be used as well.

Wovens are articles of manufacture which consist of crossed fibers, preferably fibers crossing at right angles.

Nonwovens are non-woven articles of manufacture which are composed of fibers and whose integrity is generally due to the intrinsic dinginess of the fibers. Nonwovens are preferably consolidated mechanically, for example by needling, interlooping or entangling by means of sharp jets of water or air. Nonwovens can also be consolidated adhesively or cohesively. Adhesively consolidated nonwovens are obtainable for example by interadhering the fibers with liquid binders or by melting binding fibers which were added to the nonwoven in the course of its production. Cohesively consolidated nonwovens are for example by incipiently dissolving the fibers with suitable chemicals and applying pressure.

The basis weight of the substrate materials is conveniently in the range from 20 to 800 $g/m^2$, preferably in the range from 50 to 600 $g/m^2$ and more preferably in the range from 100 to 500 $g/m^2$.

Hygroscopic substances b) are capable of absorbing water vapor; that is, water vapor from the air condenses on the hygroscopic substance, causing the water content of the hygroscopic substance b) to increase. Hygroscopic substances b) are for example inorganic salts, such as sodium chloride, lead nitrate, zinc sulfate, sodium perchlorate, chromium oxide or lithium chloride, or at least partly crystalline organic compounds, such as water-soluble polyacrylic acids. Hygroscopic inorganic salts are preferred hygroscopic substances b). Sodium chloride is most preferred.

Particularly advantageous hygroscopic substances b) are compounds where the relative humidity above a saturated aqueous solution at 20° C. equilibrates to less than 95%, preferably less than 90%, more preferably less than 85%, even more preferably less than 80% and at least 40%, preferably at least 45%, more preferably at least 50%, even more preferably at least 55% and most preferably at least 60%.

Relative humidity is the quotient of water vapor pressure and water vapor pressure multiplied by 100%.

Preferably, the hygroscopic substance b) is in a disbursed state in the on-polymerized water-absorbing polymer.

When the moisture-regulating composites of the present invention are used in seat padding for example, relative humidities above 90% are perceived as unpleasant, since the formation of sweat is favored at high atmospheric humidity. Relative humidities below 40%, however, are not advantageous either, since such low relative humidities do nothing to further enhance the seat comfort.

The moisture-regulating composites of the present invention are obtainable by polymerization of a monomer solution comprising
i) at least one ethylenically unsaturated monomer,
ii) at least one water-soluble hygroscopic substance,
iii) a crosslinker,
iv) if appropriate one or more ethylenically and/or allylically unsaturated monomers copolymerizable with the monomers mentioned under i), and
v) if appropriate one or more water-soluble polymers applied to a substrate material and polymerized, wherein the weight ratio of said hygroscopic substance ii) to said monomer i) is in the range from 0.01 to 1, said process further comprising a plasticizer being additionally included in said monomer solution.

The weight ratio of hygroscopic substance ii) to monomer i) is preferably at most, in particular less than 0.8, more preferably at most, in particular less than 0.6, even more preferably at most, in particular less than 0.5 and most preferably at most, in particular less than 0.4 and at least 0.05, more preferably at least 0.1 and even more preferably at least 0.15.

Suitable monomers i) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Preference is given to monomers i) which comprise acidic groups. Acrylic acid and methacrylic acid are particularly preferred monomers. Acrylic acid is most preferred.

The monomers i), in particular acrylic acid, comprise a hydroquinone half ether in an amount which is preferably up to 0.025% by weight. Preferred hydroquinone half ethers are hydroquinone monomethyl ether (MEHQ) and/or tocopherols.

Tocopherol refers to compounds of the following formula:

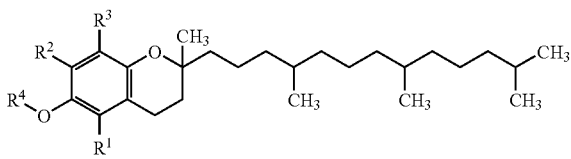

where $R^1$ is hydrogen or methyl, $R^2$ is hydrogen or methyl, $R^3$ is hydrogen or methyl and $R^4$ is hydrogen or an acid radical having 1 to 20 carbon atoms.

Preferred $R^4$ radicals are acetyl, ascorbyl, succinyl, nicotinyl and other physiologically compatible carboxylic acids. The carboxylic acids can be mono-, di- or tricarboxylic acids.

Preference is given to alpha-tocopherol where $R^1=R^2=R^3=$methyl, in particular racemic alpha-tocopherol. $R^4$ is more preferably hydrogen or acetyl. RRR-alpha-Tocopherol is preferred in particular.

The hydroquinone half ether content of the monomer solution is preferably not more than 130 weight ppm, more preferably not more than 70 weight ppm, preferably at least 10 weight ppm, more preferably at least 30 weight ppm and particularly preferably around 50 weight ppm, all based on acrylic acid, acrylic acid salts counting as acrylic acid. The monomer solution may be produced for example using an acrylic acid having an appropriate hydroquinone half ether content.

The useful hygroscopic substances ii) for the process of the present invention have already been described as hygroscopic substances b).

The water-absorbing polymers are in a crosslinked state, i.e., the polymerization is carried out in the presence of compounds ("crosslinkers") having at least two polymerizable groups capable of being free-radically interpolymerized into the polymer network so that the polymer produced comprises a corresponding fraction of the crosslinker in interpolymerized form of course. Useful crosslinkers iii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, comprise further ethylenically unsaturated groups, as described in DE-A 103 314 56 and prior German patent application 103 55 401.7, or crosslinker mixtures as described for example in DE-A 195 43 368, DE-A 196 46 484, WO 90/15830 and WO 02/32962.

Useful crosslinkers iii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl(meth) acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers iii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilizes di(meth)acrylates of polyethylene glycols, the polyethylene glycol used having a molecular weight between 300 and 1000.

However, particularly advantageous crosslinkers iii) are di- and triacrylates of 3- to 20-tuply ethoxylated glycerol, of 3- to 20-tuply ethoxylated trimethylolpropane, of 3- to 20-tuply ethoxylated trimethylolethane, especially di- and triacrylates of 2 to 6-tuply ethoxylated glycerol or of 2 to 6-tuply ethoxylated trimethylolpropane, of 3-tuply propoxylated glycerol, or of 3-tuply propoxylated trimethylolpropane, and also of 3-tuply mixedly ethoxylated or propoxylated glycerol, or of 3-tuply mixedly ethoxylated or propoxylated trimethylolpropane, of 15-tuply ethoxylated glycerol, of 15-tuply ethoxylated trimethylolpropane, and of at least 40-tuply ethoxylated glycerol, at least 40-tuply ethoxylated trimethylolethane or of at least 40-tuply ethoxylated trimethylolpropane.

Very particularly preferred crosslinkers iii) are diacrylated, dimethacrylated, triacrylated or trimethacrylated multiply ethoxylated and/or propoxylated glycerols as described for example in WO 03/104 301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels in the water-absorbing polymer (typically below weight 10 ppm) and the aqueous extracts of water-absorbing polymers produced therewith have an almost unchanged surface tension compared with water at the same temperature (typically not less than 0.068 N/m).

The crosslinker is included in the monomer solution in a customary amount of for example from 0.5 to 5.5 parts by weight based on 100 parts by weight of monomer i). In a particularly preferred embodiment, however, it is included in an amount of at least 6 parts by weight, preferably at least 7 parts by weight, more preferably at least 8 parts by weight and most preferably at least 9 parts by weight, all based on the 100 parts by weight of monomer i). The upper limit of the crosslinker content in the monomer is less critical in that generally a crosslinker content of not more 25 parts by weight, preferably not more than 20 parts by weight and more preferably not more 18 parts by weight is used. Examples of suitable crosslinker contents are at least 10 parts by weight, at least 10.5 parts by weight, at least 11 parts by weight, at least 11.5 parts by weight, at least 12 parts by weight, at least 12.5 parts by weight, at least 13 parts by weight based on 100 parts by weight of monomer i).

Examples of ethylenically unsaturated monomers iv) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers v) include polyvinyl alcohol, polyvinylpyrrolidone, starch, starch derivatives, polyglycols or polyacrylic acids preferably polyvinyl alcohol and starch.

Hygroscopic polymers, such as soluble polyacrylic acids, can be used not only as hygroscopic substance ii) but also as water-soluble polymer v).

When customary graft polymerization catalysts, for example iron salts, are added to the monomer solution, then the polymers will serve as a grafting base for the polymerization and the monomers to be polymerized will become grafted onto the polymers. When no graft polymerization catalysts are used, then the polymers will survive the polymerization in a substantially unaltered state and act as a hygroscopic substance.

The acid groups of the preferred monomers i) are typically in a partly neutralized state, their degree of neutralization being preferably in the range from 25 to 95 mol %, more preferably in the range from 40 to 90 mol %, even more preferably in the range from 50 to 80 mol % and most preferably in the range from 60 to 80 mol %. Customary neutralizing agents can be used, preference being given to alkali metal hydroxides, alkali metal oxides, alkali metal carbonates or alkali metal bicarbonates and also mixtures thereof. Ammonium salts can be used instead of alkali metal salts. Sodium and potassium are particularly preferred as alkali metals, but most preferred are sodium hydroxide, sodium carbonate or sodium bicarbonate and also mixtures thereof.

The neutralization is typically achieved by admixing the neutralizing agent as an aqueous solution, as a melt or else preferably as a solid. For example, sodium hydroxide having a water content of distinctly below 50% by weight can be present as a waxy mass having a melting point of above 23° C. In this case, metering in the piece or as a melt at elevated temperature is possible.

The aqueous monomer solution is applied, preferably by spraying, to the substrate material. Useful substrate materials have already been described as substrate material a).

Subsequently, the monomer solution on the substrate material is polymerized and the composite dried. The polymerization is preferably induced by UV radiation and/or thermally. As is customary for such polymerization reactions, an initiator can be used to hasten or police the start of the polymerization reaction; any known initiator or initiator system may be used here in a conventional manner.

The polymers c) comprise at least one plasticizer which is included in the monomer solution before polymerization and remains in the polymer. A plasticizer is herein to be understood as meaning a substance that, in the amount used, lowers the glass transition temperature of the polymer c). The amount of plasticizer used will generally lower the glass transition temperature of the polymer by at least 2° C., preferably by at least 4° C., more preferably by at least 6° C. and most preferably by at least 10° C. For example, a plasticizer is included in an amount which will lower the glass transition temperature of the polymer by at least 20° C. or by at least 30° C. The glass transition temperature is a known property of polymers and can be measured by the ASTM E1356-03 "Standard Test Method for Assignment of the Glass Transition Temperatures by Differential Scanning Calorimetry" or the equivalent ISO 11357-2 standard.

Customary plasticizers are liquid at room temperature and are also solvents or dispersants for the polymer. When the polymer is produced by UV irradiation of the monomer, a plasticizer that is sufficiently stable to UV light and moreover does not disrupt the UV-induced polymerization must be chosen. Preferably, the plasticizer is hydrophilic and miscible with water in any proportion. Examples of suitable plasticizers are alcohols, polyalcohols such as glycerol and sorbitol, glycols and ether glycols such as mono- and diethers of polyalkylene glycols, mono- or diesters of polyalkylene glycols, polyethylene glycols, polypropylene glycols, mixed polyethylene or polypropylene glycols, glycolates, glycerol, sorbitan esters, citric or tartaric esters or imidazoline-derived amphoteric surfactants. Preferred plasticizers are polyalcohols such as glycerol and sorbitol, polyethylene glycol and mixtures thereof. Glycerol is particularly preferred.

Useful plasticizers further include hydrocarbons and hydrocarbon mixtures such as white oil, in particular medicinal white oil or liquid paraffin.

The plasticizer is typically included in a sufficient amount to achieve the desired lowering in the glass transition temperature. Typical plasticizer contents are 5-50 parts by weight, preferably 8-40 parts by weight and especially 10-30 parts by weight of plasticizer based on 100 parts by weight of monomer i).

The composites of the present invention are very useful for moisture regulation, in particular in mattresses and seat padding, for example in automotive seats.

Seat pads or mattresses comprising the composites of the present invention enhance the seating or lying comfort by regulating the relative atmospheric humidity to a pleasant degree and preventing excessive sweating. At the same time, the composites of the present invention are capable of optimally releasing the sorbed moisture again in phases of nonuse and of rapidly regenerating themselves. Owing to this balanced profile of properties, the composites of the present invention provide an hitherto unachieved sitting or lying comfort.

Methods:

Determination of Moisture Uptake

The composites were conditioned at a temperature of 23° C. and a relative humidity of 50% for 60 minutes until equilibration. The relative humidity was then raised to 90% and the composites held at 30° C. for 90 minutes (absorption phase). Thereafter, the relative humidity was lowered to 40% and the sample held at 40° C. for 100 minutes (desorption phase).

The weight change due to absorption/desorption is continuously measured and as a weight increase based on g of applied substance (water-absorbing polymer and/or salt). The reference point for the weight increase is the weight following 60 minutes of equilibration.

EXAMPLES

Example 1

A polyethylene terephthalate nonwovens having a basis weight of 70 g/m$^2$ was sprayed with a monomer solution before curing by means of UV radiation for 2 minutes. This was followed by drying at 90° C. in a countercurrent dryer for 5 minutes.

The monomer solution comprised 19 599 g of a 37.5% by weight aqueous sodium acrylate solution (corresponding to 24.5% by weight of sodium acrylate in the entire monomer solution), 435 g of acrylic acid (8.5% by weight), 900 g of polyethylene glycol diacrylate (diacrylate of a polyethylene glycol having an average molar mass of 400) (3% by weight) as a crosslinker, 66 g of 2-hydroxy-1-[4-(hydroxyethoxy) phenyl]-2-methyl-1-propanone (0.22% by weight) as an initiator, 1500 g of glycerol (5% by weight) and 7500 g of a 25% by weight aqueous sodium chloride solution (6.25% by weight of NaCl).

The amount of monomer solution was chosen so that the loading of the polyethylene terephthalate nonwovens with on-polymerized water-absorbing polymer was 160 g/m$^2$.

We claim:

1. A moisture-regulating composite comprising
   a) at least one sheet substrate material
   b) at least one water-soluble hygroscopic substance
   c) at least one water-absorbing polymer polymerized onto said substrate material a) in the presence of said substance b),
   the weight ratio of said hygroscopic substance b) to said polymer c) being in the range of 0.01 and 1, wherein said polymer c) additionally comprises a plasticizer.

2. The composite according to claim 1 wherein said substrate material a) is a woven fabric and/or nonwoven.

3. The composite according to claim 1 wherein a relative humidity above a supersaturated aqueous solution of said hygroscopic substance b) in equilibrium at 20° C. is at least 40%.

4. The composite according to claim 1 wherein said hygroscopic substance b) is an inorganic salt.

5. The composite according to claim) wherein said polymer c) comprises acidic groups.

6. The composite according to claim 5 wherein said acidic groups are at least 25 mol % neutralized.

7. A seat padding comprising a composite according to claim 1.

8. A mattress comprising a composite according to claim 1.

9. A process for producing a moisture-regulating composite, which comprises a monomer solution comprising
   i) at least one ethylenically unsaturated monomer,
   ii) at least one water-soluble hygroscopic substance
   iii) a crosslinker
   iv) optionally one or more ethylenically and/or allylically unsaturated monomers copolymerizable with the monomer i), and
   v) optionally one or more water-soluble polymers being applied to a sheet substrate material and polymerized, the weight ratio of said hygroscopic substance ii) to said monomer i) being between 0.01 and 1, said process further comprising a plasticizer being additional included in said monomer solution.

10. The process according to claim 9 wherein said monomer comprises acidic groups.

11. The process according to claim 10 wherein said acidic groups are at least 25 mol % neutralized.

12. The process according to claim 9 wherein a relative humidity above a supersaturated aqueous solution of said hygroscopic substance ii) in equilibrium at 20° C. is at least 40%.

13. The process according to claim 9 wherein said hygroscopic substance ii) is an inorganic salt.

14. The process according to claim 9 wherein said substrate material is a woven fabric and/or nonwoven.

* * * * *